United States Patent [19]

Buckholtz et al.

[11] 3,989,715

[45] Nov. 2, 1976

[54] PROCESS FOR MANUFACTURING CHLOROTHIANTHRENES

[75] Inventors: Harry E. Buckholtz, Kenmore; Arun C. Bose, Tonawanda, both of N.Y.; John C. Graham, Warren, Mich.

[73] Assignee: Hooker Chemicals & Plastics Corporation, Niagara Falls, N.Y.

[22] Filed: Aug. 1, 1975

[21] Appl. No.: 601,218

[52] U.S. Cl. .......................... 260/327 P; 260/650 R
[51] Int. Cl.² ..................................... C07D 339/08
[58] Field of Search ..................... 260/327 P, 340.3

[56] References Cited
FOREIGN PATENTS OR APPLICATIONS 1,222,508   8/1966   Germany ............................ 260/327

OTHER PUBLICATIONS

Olah, Friedel–Crafts & Related Reactions (Interscience, N.Y., 1964), vol. III, p. 1554.

*Primary Examiner*—Natalie Trousof
*Assistant Examiner*—C. M. S. Jaisle
*Attorney, Agent, or Firm*—Peter F. Casella; William J. Crossetta, Jr.

[57] ABSTRACT

Thianthrene in monochlorotoluene, is reacted with excess chlorine in the presence of a Lewis acid catalyst, to yield a mixture of chlorothianthrenes, the major component of which is 2,3,7,8-tetrachlorothianthrene. Recrystallization of the chlorothianthrene mixture from a suitable solvent, such as tetrahydrofuran yields 2,3,7,8-tetrachlorothianthrene of greater than 90 percent purity.

12 Claims, No Drawings

PROCESS FOR MANUFACTURING CHLOROTHIANTHRENES

BACKGROUND OF THE INVENTION

This invention relates to the manufacture of chlorothianthrenes and in particular to the manufacture of 2,3,7,8-tetrachlorothianthrene, in substantially pure form or as a component of a chlorothianthrene mixture. Chlorothianthrenes, especially the compound 2,3,7,8-tetrachlorothianthrene are useful as paradirecting nuclear chlorination catalysts for toluene. Further details regarding chlorothianthrenes, especially 2,3,7,8-tetrachlorothianthrene and the use thereof with a Lewis acid catalyst as a chlorination catalyst may be found in copending application Ser. No. 601,219 (Case 3387), filed Aug. 1, 1975, the disclosure of which is hereby incorporated by reference. The preparation of thianthrene and various derivatives thereof including halogenated thianthrenes, are known in the art. It is known for example, to prepare such halogenated derivatives as 1-chloro, 2-chloro-, 2,7-dichloro-, 2-bromo-, 2,6-dibromo-, and the like from thianthrene directly or from other raw materials by indirect routes. The preparations of 2,3,7,8-tetrabromothianthrene by reaction of bromine and thianthrene is disclosed by Gilman et al. *J Org. Chem.* 23 (1958) pp. 313–314. According to the method of Gilman et al. bromine was reacted directly with thianthrene, the product treated with glacial acetic acid and the resultant suspension refluxed for 16 hours, treated with a dilute solution of sodium thiosulfate, filtered, washed with water, and dried. The resultant crude product was recrystallized twice from xylene with a final yield of 41 percent. The emphasis, in the literature directed to halogenated derivatives of thianthrene, has been toward laboratory preparations. Little or no attention has been directed to the development of practical processes for the commercial production of halogenated thianthrenes. Furthermore, the preparation of the compound 2,3,7,8-tetrachlorothianthrene, to which one aspect of the present invention is directed, is not disclosed in the prior art.

Accordingly, it is an object of the present invention to provide a process for manufacturing chlorothianthrenes that is direct and simple and readily adaptable to large scale commercial operations. It is a further object to provide a process for the manufacture of chlorothianthrene mixtures having as a major component thereof 2,3,7,8-tetrachlorothianthrene. It is a further object to provide a method of preparation of the compound 2,3,7,8-tetrachlorothianthrene. It is a still further object to provide novel and useful compositions comprising chlorothianthrene mixtures having as a major component thereof 2,3,7,8-tetrachlorothianthrene.

The thianthrene compounds prepared in accordance with the present invention are described herein in accordance with the current chemical Abstracts system whereby the numbering of ring positions is as follows:

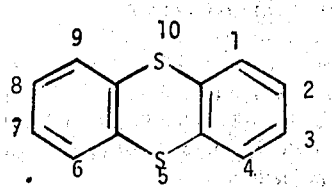

SUMMARY OF THE INVENTION

We have now found that chlorothianthrene mixtures, having as a component thereof, 2,3,7,8-tetrachlorothianthrene may be manufactured by reacting a stoichiometric excess of chlorine with thianthrene in monochlorotoluene, in the presence of a Lewis acid catalyst. The process is simple and direct and readily adaptable to large scale commercial production, either as a batch type or continuous reaction. The chlorination reaction may be effected, for example, by bubbling gaseous chlorine into the solution of thianthrene in monochlorotoluene, preferably with stirring.

A wide variety of known Lewis acid catalysts may be employed in the process of the present invention. Suitable catalysts for this purpose include, for example, compounds of antimony, lead, iron, molybdenum and aluminum, such as the halides, oxyhalides, oxides, sulfides, sulfates, acids, carbonyls or elemental form of these elements and mixtures of such compounds. Typical of the catalysts which may be employed in the process of this invention are aluminum chloride, antimony trichloride, antimony pentachloride, antimony trioxide, antimony tetraoxide, antimony pentaoxide, antimony trifluoride, antimony oxychloride, antimony sulfide, molybdenum carbonyl, lead sulfide, ferric chloride, ferrous chloride, ferrous sulfate, ferric oxide, ferrous sulfide, iron disulfide, iron metal, and the like. The preferred Lewis acid catalysts are the sulfides, oxides, and chlorides of antimony or iron. The amount of catalyst may vary considerably but is preferably in the range of about 1.0 to about 2.5 percent by weight based on the amount of thianthrene.

In the chlorination of thianthrene in accordance with the process of this invention, chlorine substitution occurs preferentially at the thianthrene ring positions para to the sulfur atoms, that is, at the 2,3,7, and 8 positions. Thus the chlorothianthrene mixtures prepared may be predominently mixtures of 2-chloro-, 2,7-dichloro-, 2,3,7-trichloro-, 2,3,8-trichloro- and 2,3,7,8-tetrachlorothianthrene, depending on the degree of chlorination, with little or no chlorine substitution occurring at the peri-positions, that is the 1,4,6 and 9 positions until the chlorination is carried to a degree required for the formation of hexachloro and higher chlorothianthrenes.

An important aspect of the present invention resides in the use of monochlorotoluene as the solvent for the chlorination reaction medium. It will be recongnized by those skilled in the art, that the solvent itself, that is, monochlorotoluene, is susceptible to reaction with chlorine under the reaction conditions described hereinabove. Thus a portion of the chlorine entering the reaction medium is consumed by the solvent to form dichlorotoluene. Typically, in the process of the present invention, between about 10 and 50 percent of the monochlorotoluene will be converted to dichlorotoluene. In an attempt to avoid the seeming disadvantage of a chlorine-reactive solvent, various other solvents, especially more highly chlorinated solvents such as $CCl_4$, $CHCl_3$ and the like have been tried. It has been found, surprisingly, that when such other solvents are employed, little or no 2,3,7,8-tetrachlorothianthrene is produced. On the other hand, when monochlorotoluene is employed as the solvent, relatively high yields of the desired 2,3,7,8-tetrachlorothianthrene are achieved.

The monochlorotoluene solvent may be ortho-, meta-, or parachlorotoluene or a mixture thereof. The amount of thianthrene present in the reaction medium may vary considerably and may be present either in the soluble phase or, at higher concentrations, as a slurry, with agitation during the chlorination reaction. It is preferred that the thianthrene be present in the soluble phase.

Due to the susceptibility of the solvent to chlorination, it is preferred to employ excess chlorine to achieve high yields of 2,3,7,8-tetrachlorothianthrene. Most preferably the amount of chlorine supplied to the reaction is about 50 to about 100 percent excess of the stoichiometric amount based on the conversion of thianthrene to tetrachlorothianthrene. Under these conditions, chlorothianthrenes may be recovered in yields greater than 50 percent, based on the thianthrene starting material, with 2,3,7,8-tetrachlorothianthrene present in amounts of about 50 to 75 percent of the chlorothianthrene product. Chlorothianthrene solids may be readily removed from the reaction mixture, for example, by filtration. Dissolved chlorothianthrene product and the reaction solvent may be conveniently separated by known methods such as distillation. By recrystallization of the product from a suitable solvent, such as xylene or tetrahydrofuran, 2,3,7,8-tetrachlorothianthrene product having a purity greater than 90 percent may be attained.

Under atmospheric pressure, the process of the present invention may be carried out over a wide range of temperatures, ranging for example, from sub-zero temperatures (Celsius scale) to 150° Celsius or higher, the upper limit being determined by the boiling point of the reaction mixture. However, we have found that at higher temperatures the chlorination of monochlorotoluene to dichlorotoluene is increased. Accordingly, it is preferred to maintain a reaction temperature in the range of about 50° to about 100° Celsius and most preferably about 55° to about 85° Celsius. Although it is preferred to carry out the process at atmospheric pressure, subatmospheric and superatmospheric pressure may be employed if desired.

The following examples illustrate our invention, but it is to be understood that the specific details given in the examples have been chosen for the purpose of illustration and are not intended to limit our invention. In the examples, unless otherwise indicated all parts and percentages are by weight and all temperatures are in degrees Celsius.

The following experiment describes the preparation of chlorothianthrene by reacting thianthrene with chlorine at 60° C in the presence of SbCl₃ catalyst in monochlorotoluene as the solvent.

EXAMPLE 1

Twenty parts of thianthrene dissolved in 142 parts of monochlorotoluene (a commercial mixture of about 50 percent ortho- and 50 percent para-chlorotoluene) were charged to a batch type stirred tank reactor together with 0.2 part of $SbCl_3$. Chlorine was fed to the reaction mixture at about 0.35 parts/min. for a 4 hour period. The mixture was then cooled and 14.5 parts of chlorothianthrene were obtained which had 68.03 percent 2,3,7,8-tetrachlorothianthrene. Part of this sample was recrystallized from tetrahydrofuran to produce 95.3 percent 2,3,7,8-tetrachlorothianthrene, melting point 250°–255° C. Another 3.7 parts were recovered as a second crop from the mother liquor, giving a total yield of 19.2 parts of chlorothianthrene. This second crop was low melting with 43.25 percent of the 2,3,7,8-isomer indicating that the composition was a mixture of 2-chloro-, 2,7-dichloro-, and other isomers with 2,3,7,8-tetrachlorothianthrene.

It will be apparent to those skilled in the art that the maintenance of the product in soluble phase may offer considerable advantage in material handling, for example, the transport through pipelines, as well as the advantage of providing the product in dissolved form for subsequent use. The following example relates to the preparation of chlorothianthrene directly from the thianthrene in solution in monochlorotoluene and also retaining the resultant product in soluble phase.

EXAMPLE 2

Approximately 780 parts of a solution containing 25.20 parts thianthrene in monochlorotoluene was charged to a reaction vessel together with about 0.2 percent of FeS (50–100 mesh particle size) as catalyst. A total of 57 parts of chlorine was fed slowly into the reaction mixture while temperature of the reaction mixture was maintained at about 58° C. The resulting liquor contained 19 parts 2,3,7,8-tetrachlorothianthrene, representing a yield of 46.5 percent, based on thianthrene starting material.

In the preparation of chlorothianthrenes from thianthrene by the process of the present invention, thianthrene has been considered a limiting reactant and chlorine as an excess reactant. In the following example, it is shown that 50–100 percent excess of the stoichiometric amount of chlorine is desirable. This example will also illustrate the use of $Sb_2O_3$ as the catalyst. It also indicates that higher reaction temperatures improve chlorine absorption rate.

EXAMPLE 3

Part A

A solution of 20 parts of thianthrene dissolved in 320 parts of monochlorotoluene was charged to a reaction vessel together with 0.4 part of $Sb_2O_3$. In order to improve chlorine absorption, the reactor temperature was maintained at 75° C. Stoichiometric amount (26.4 parts) of chlorine was sparged to the system and an analysis of the resultant solution indicated only 0.249 parts of tetrachlorothianthrene in 100 parts of solution.

Part B

The reaction mixture was maintained at about 75° C while a 100 percent excess of chlorine was added. The reaction mixture was then cooled and filtered, yielding 7.51 parts of solid and 336.7 parts of filtrate. Analysis of the solid product indicated 4.08 parts (67.6 percent) of the 2,3,7,8-tetrachlorothianthrene isomer.

Analysis of the filtrate indicated 8.56 parts (2.54 percent) of the 2,3,7,8-tetrachlorothianthrene isomer.

Part C

The procedure of Part A was repeated except that the amount of chlorine charged to the reaction mixture was 39.6 parts, representing a 50 percent excess of the stoichiometric amount. The reaction product consisted of 3.6 parts of solid containing 59.31 percent (2.14 parts) of the 2,3,7,8-tetrachlorothianthrene isomer and 339.0 parts of filtrate containing 2.11 percent (7.16 parts) of the isomer.

Part D

A portion of the solid chlorothianthrene mixture of Part B, containing 67.62 percent 2,3,7,8-tetrachlorothianthrene isomer was recrystallized from tetrahydrofuran. The resultant product, representing a net recovery of 72% of the portion recrystallized, was 90.75% pure with a melting point of 268°–272° C. An NMR analysis further confirmed the existence of 2,3,7,8-tetrachlorothianthrene in a very pure state.

Example 4 relates to using $Fe_2O_3$ as the catalyst system for making chlorothianthrene.

EXAMPLE 4

Part A

To a solution of 20 parts of thianthrene dissolved in 320 parts of monochlorotoluene was added 0.32 part of $Fe_2O_3$. Following the procedure of the preceding example, chlorine gas was added and reacted in 100 percent excess of the stoichiometric amount to yield 5.9 parts of solid containing 70.12 percent 2,3,7,8-tetrachlorothianthrene isomer and 344.3 parts filtrate containing 8.85 parts of the isomer or a total yield of 14.95 parts of the desired isomer.

Part B

In a similar experiment using 20 parts of thianthrene in 444 parts of monochlorotoluene solvent, only 2.28 parts of solid were recovered containing 65.37 percent 2,3,7,8-tetrachlorothianthrene and 447.8 parts of filtrate were recovered containing 9.29 parts of the isomer.

It may be seen that the amount of solvent may be adjusted to yield a greater or lesser amount of product in the soluble phase. In the foregoing example, when the amount of solvent is increased to provide a concentration of about 5 percent thianthrene (Part 4B) a greater percentage of the product 2,3,7,8-tetrachlorothianthrene is retained in the soluble phase.

The sample of solid containing 65.37 percent tetrachlorothianthrene (part B) was recrystallized from tetrahydrofuran. The recrystallized product was 93.73 percent pure 2,3,7,8-tetrachlorothianthrene.

As disclosed hereinabove, the use of monochlorotoluene as the solvent in the process of the present invention results in a portion of the chlorine reactant being consumed by the solvent, in the formation of dichlorotoluene. In an attempt to overcome this problem, various other solvents, especially more highly chlorinated solvents, such as $CCl_4$ and $CHCl_3$ were tried in substitution for monochlorotoluene. Thus, in Example 5, below, the general procedure of the preceding example was followed, except that $CCl_4$ was employed as the solvent.

EXAMPLE 5

To a solution of 20 parts of thianthrene dissolved in 225.3 parts of $CCl_4$ was added 0.2 part of $SbCl_3$. The solution was maintained at about 60° C while 48 parts of chlorine were added. The reaction product was 5.0 parts of solid (m.p. 96°–99° C) containing none of the desired 2,3,7,8-tetrachlorothianthrene.

The procedure of Example 5 was repeated except that $CHCl_3$ was substituted for $CCl_4$. None of the desired 2,3,7,8-tetrachlorothianthrene was produced.

Example 6, below, demonstrates the use of $FeCl_3$ as a catalyst in the process of the present invention.

EXAMPLE 6

To a solution of 20 parts of thianthrene dissolved in 444 parts of monochlorotoluene was added 0.4 part of $FeCl_3$. The reaction mixture was charged to a stirred, batch type reactor and heated to 75° C. The temperature was maintained at 75° C while a total of 58.2 parts of chlorine were sparged subsurface over a period of about 4 and one-half hours. The resultant solution was analyzed and found to contain about 15 parts of 2,3,7,8-tetrachlorothianthrene.

It will be seen that the foregoing description and examples provide a simple and effective method for the production of chlorothianthrenes, especially 2,3,7,8-tetrachlorothianthrene, on a commercial scale. The foregoing specification is intended to illustrate the invention with certain preferred embodiments, but it is understood that the details disclosed herein can be modified without departing from the spirit and scope of the invention.

We claim:

1. A process for the manufacture of chlorothianthrene which comprises reacting chlorine with thianthrene in monochlorotoluene in the presence of a Lewis acid catalyst.

2. A process for the manufacture of chlorothianthrene which comprises reacting chlorine with thianthrene in monochlorotoluene in the presence of a Lewis Acid catalyst selected from the groups consisting of $Sb_2O_3$, $SbCl_3$, FeS, $Fe_2O_3$ and $FeCl_3$.

3. A process according to claim 2 wherein the amount of chlorine is at least about 50 percent stoichiometric excess of the theoretical amount required for the formation of tetrachlorothianthrene.

4. A process according to claim 3 which additionally comprises recovering the chlorothianthrene product as a mixture of chlorothianthrenes having as the major component thereof, 2,3,7,8-tetrachlorothianthrene.

5. A process according to claim 4 wherein 2,3,7,8-tetrachlorothianthrene is recovered from the mixture of chlorothianthrenes.

6. A process according to claim 5 wherein the mixture of chlorothianthrenes is recrystallized from tetrahydrofuran to yield 2,3,7,8-tetrachlorothianthrene.

7. A process according to claim 3 wherein the catalyst is $SbCl_3$.

8. A process according to claim 3 wherein the catalyst is FeS.

9. A process according to claim 3 wherein the catalyst is $Sb_2O_3$.

10. A process according to claim 3 wherein the catalyst is $Fe_2O_3$.

11. A process according to claim 3 wherein the catalyst is $Fe_2O_3$.

12. A process according to claim 3 wherein chlorine is supplied to the reaction in an amount of between about 50 percent and 100 percent stoichiometric excess of the theoretical amount required for the formation of tetrachlorothianthrene.

* * * * *

UNITED STATES PATENT OFFICE
CERTIFICATE OF CORRECTION

PATENT NO. : 3,989,715
DATED : November 2, 1976
INVENTOR(S) : Harry E. Buckholtz, Arun C. Bose and John C. Graham It is certified that error appears in the above-identified patent and that said Letters Patent are hereby corrected as shown below:

Column 6, line 58, "$Fe_2O_3$" should read ---$FeCl_3$---.

Signed and Sealed this

Fifth Day of April 1977

[SEAL]

Attest:

RUTH C. MASON
*Attesting Officer*

C. MARSHALL DANN
*Commissioner of Patents and Trademarks*